United States Patent
Elmaleh

(10) Patent No.: US 10,238,820 B2
(45) Date of Patent: *Mar. 26, 2019

(54) DRY-POWDER INHALATION DEVICE

(71) Applicant: David R. Elmaleh, Newton, MA (US)

(72) Inventor: David R. Elmaleh, Newton, MA (US)

(73) Assignee: Seroton, Inc., Boston, MA (US)

( * ) Notice: Subject to any disclaimer, the term of this patent is extended or adjusted under 35 U.S.C. 154(b) by 300 days.

This patent is subject to a terminal disclaimer.

(21) Appl. No.: 14/150,268

(22) Filed: Jan. 8, 2014

(65) Prior Publication Data

US 2015/0190594 A1 Jul. 9, 2015

(51) Int. Cl.
*A61M 15/00* (2006.01)

(52) U.S. Cl.
CPC .... *A61M 15/0035* (2014.02); *A61M 15/0003* (2014.02); *A61M 15/004* (2014.02); *A61M 2202/064* (2013.01); *A61M 2205/19* (2013.01)

(58) Field of Classification Search
CPC ............ A61M 15/0028; A61M 15/004; A61M 11/003; A61M 11/0031; A61M 11/0033; A61M 11/0035; A61M 15/0003; A61M 15/0008; A61M 15/0091; A61M 15/06; A61M 2202/064; A61M 2205/19
USPC ............. 128/203.15, 203.12, 203.21, 203.26
See application file for complete search history.

(56) References Cited

U.S. PATENT DOCUMENTS

| | | |
|---|---|---|
| 3,991,761 A | 11/1976 | Cocozza |
| 7,077,130 B2 | 7/2006 | Nichols et al. |
| 2001/0007853 A1 | 7/2001 | Dimarchi et al. |
| 2001/0053761 A1 | 12/2001 | Dimarchi et al. |
| 2004/0154618 A1 | 8/2004 | Edwards et al. |

(Continued)

FOREIGN PATENT DOCUMENTS

| | | |
|---|---|---|
| EP | 0 385 156 B1 | 9/1990 |
| EP | 0 558 879 B1 | 9/1993 |

(Continued)

OTHER PUBLICATIONS

Wolff et al., "Generation of Aerosolized Drugs", J. Aerosol. Med. pp. 89-106 (1994).

(Continued)

*Primary Examiner* — Gregory Anderson
*Assistant Examiner* — Elliot S Ruddie
(74) *Attorney, Agent, or Firm* — Pearl Cohen Zedek Latzer Baratz LLP

(57) ABSTRACT

An improved dry-powder inhalation device having a casing having an air inlet located at a first terminus; a powder delivery port located at a second terminus, which is positioned distal to the air inlet; and an elongated support panel located within an interior of the casing and being fitted within the casing so as to partially rotate therein about a single axis. The support panel has at least one compartment containing dry-powder located proximally to the second terminus, and the casing has a plurality of needle-like structures located proximal to the delivery port and arranged above the dry-powder compartment. The compartment with a dry-powder includes a blister structure encasing the dry-powder, whereby airflow through the device causes the elongated support panel to partially rotate repeatedly within the casing, thereby striking the plurality of needle-like structures and releasing the dry-powder in the airflow.

12 Claims, 5 Drawing Sheets

(56) References Cited

U.S. PATENT DOCUMENTS

Figure 1:
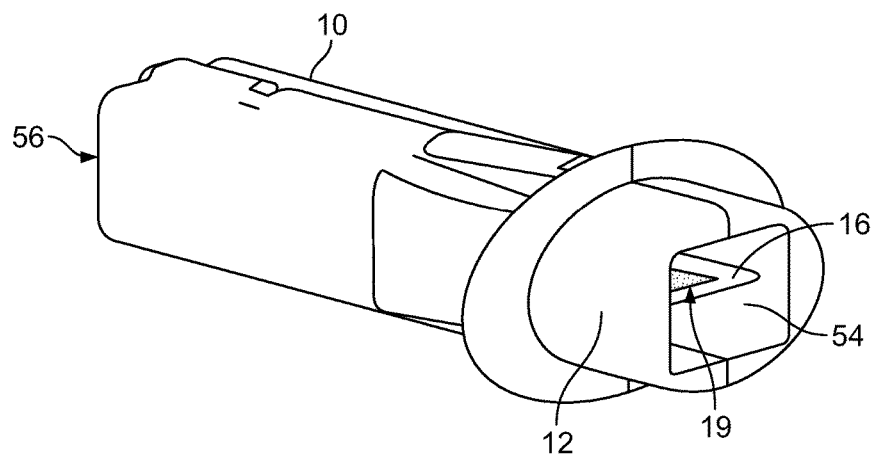

| | | | |
|---|---|---|---|
| 2007/0283955 A1 | 12/2007 | Tsutsui | |
| 2010/0051023 A1 | 3/2010 | Kladders | |
| 2011/0220106 A1 | 9/2011 | Ganem et al. | |
| 2013/0042864 A1* | 2/2013 | Adler | A61M 15/0028 128/203.15 |
| 2013/0061851 A1* | 3/2013 | Jones | A61M 15/0028 128/203.15 |
| 2014/0150787 A1 | 6/2014 | Ellwanger et al. | |
| 2015/0190595 A1* | 7/2015 | Elmaleh | A61M 15/0035 128/203.15 |

FOREIGN PATENT DOCUMENTS

| | | |
|---|---|---|
| EP | 0 629 136 B1 | 12/1994 |
| EP | 0 973 570 B1 | 1/2000 |
| WO | WO 92/004069 A1 | 3/1992 |
| WO | WO 93/017728 A1 | 9/1993 |
| WO | WO 98/034663 | 8/1998 |
| WO | WO 02/055142 A2 | 7/2002 |
| WO | WO 08/124666 A2 | 10/2008 |
| WO | WO 2011/080747 A2 | 7/2011 |
| WO | WO 2014/006135 A2 | 1/2014 |

OTHER PUBLICATIONS

Wagenseil, L. et al., "Optimization and performance of the resQhaler—a single-use disposable dry powder inhaler", Drug Delivery to the Lungs 22, Christian-Albrechts-Universitat zu Kiel, Edinburgh, Scotland, 2011.

Aespira Investor Presentation, "Breathing new life in healthcare", 2013.

International Search Report for International Application No. PCT/US2015/010506, dated May 1, 2015.

Search Report of European Application No. EP 15 73 5379, dated Jun. 28, 2017.

Office Action for U.S. Appl. No. 14/518,487 (points 5 and 13), dated Mar. 9, 2018.

Office Action of Japanese Application No. JP2016-545994 dated Nov. 27, 2018.

* cited by examiner

DRY-POWDER INHALATION DEVICE

FIELD OF THE INVENTION

The present invention relates to improvements to dry-powder inhalers for the treatment of respiratory diseases and systemic drug delivery via deep lung access.

BACKGROUND OF THE INVENTION

Numerous drugs, medications and other substances are inhaled into the lungs for rapid absorption in the blood stream and systemic delivery, or alternatively for therapeutic treatment locally. Inhaled drugs are typically either in aerosolized or powder form. In either case, the delivered agent should have a particle or droplet nuclei size that is 5 microns or less in order to reach the terminal ramifications of the respiratory tree.

Such small particles are, however, thermodynamically unstable due to their high surface area to volume ratio, which provides significant excess surface free energy and encourages particles to agglomerate. Agglomeration of the particles, and adherence of the particles to the internal surfaces of the inhaler, result in delivery of particles that are too large in size, delivery of a lower dose due to particles adhering to the interior surfaces of the inhaler, and poor flow and non-uniform dispersion resulting in the delivery of a varying dosage. In addition, as noted above, many dry-powder formulations employ larger excipient particles to promote flow properties of the drug. However, separation of the drug from the excipient, as well as the presence of agglomeration, can require additional inspiratory effort, which, again, can impact the stable dispersion of the powder within the air stream of the patient. Unstable dispersions may inhibit the drug from reaching its preferred deposit/destination site and can prematurely deposit undue amounts of the drug elsewhere.

Further, the hygroscopic nature of many dry-powder drugs may also require that the device be cleansed (and dried) at periodic intervals.

U.S. Patent Application Publication No. 2013/0042864, filed Oct. 3, 2012, which is hereby incorporated herein by reference in its entirety, describes a dry-powder inhaler including a casing having an air inlet located at a first terminus, a powder delivery port located at a second terminus and positioned distal to the air inlet, and an elongated assembly located within the interior of the casing. A first assembly terminus is located proximally to the air inlet, and a second assembly terminus is located proximally to the powder delivery port. The elongated assembly is fitted within the casing such that the assembly partially rotates within the casing about a single axis, and said elongated assembly comprises at least one compartment containing a dry-powder and located proximally to the second assembly terminus. The dry-powder compartment includes a porous structure encasing the dry-powder; whereby airflow through the device causes the assembly to partially rotate or pivot within the casing about a single axis, and dry-powder is thereby released from the compartment and becomes entrained in the airflow.

However, it is important to provide a single use (disposable) dry-powder inhalation device that facilitates the dispersion of active drug powder and delivers a consistent dose to the lung for respiratory disease treatment or the deep lung for systemic drug delivery. Many inhalation devices, such as described in U.S. Patent Application Publication No. 2013/0042864, require a mesh to be arranged over the dry-powder compartment and an additional film to be placed over the mesh in order to hermetically seal the compartment from air and prevent loss of the drug by movement or transport. Unfortunately, the process of filling the compartment, placing the mesh over the compartment and placing the film over the mesh is expensive and slow. Furthermore, the film is attached by glue or press, and must be pulled from over the cavity before use. However, pulling the film will twist the thin elongated assembly and disrupt its delicate rotating operation. Furthermore, developing an appropriate removable system and assembling it is integrated part of the inhalation device is expensive and will require careful complicated operating instructions.

Therefore, a need exists for improved disposable, single dose, dry-powder inhalation device that facilitates the dispersion of active drug powder and delivers a consistent dose to the lung, and that does not utilize mesh, cover film, glue or other means to seal the dry powder compartment.

In addition, a need exists for an improved single dose disposable dry-powder inhalation device that facilitates the dispersion of active drug powder and delivers a consistent dose to the lung the inhaler, but that does not require pushing, pulling or twisting of the inhalation device or of any of its components in order to withdraw the active drug powder from the dry powder compartment.

SUMMARY OF THE INVENTION

Accordingly, it is the object of the present invention to provide an improved dry-powder inhalation device which obviates the need to use a mesh and film to cover the dry-powder compartment. Without the mesh and the film, the improved dry-powder inhaler has a greatly reduced cost of packaging and assembly, as well as, cost of operation and development.

It is an object of the present invention to provide an improved dry-powder inhalation device in which the dry-powder compartment is covered with a simple blister-type cover. Such blister-type covers may be composed of a material, for example, aluminum, aluminum foil or other suitable material, which may be easily punctured or ruptured.

It is another object of the present invention to simplify the assembly of typical dry-powder inhalation devices, such that filling of the dry-powder compartment with the active drug powder and covering/sealing of the filled dry-powder compartment can be done inexpensively and quickly, while still being done hermetically.

It is a further object of the present invention to simplify the withdrawal of the active drug powder from the dry-powder compartment by eliminating the need for a mesh and a mesh cover, as in the above-mentioned dry-powder inhalation devices. The uncovering or opening of the herein described dry-powder compartment and withdrawal of the active drug powder does not cause twisting or pulling and improper operation of the inhaler.

In accordance with these and other objects of the invention, the invention relates to a dry-powder inhalation device whose dry-powder compartment is covered with a puncturable covering, such as aluminum or other known blister-pack type coverings, and sealed as known in the art. In addition, a region on an interior portion of the casing includes one or more fins, pins, edges, or other type of sharp or pointed needle- or pin-like structures. This region is arranged over or proximal to, and in alignment with, the puncturable covering of the dry-powder compartment, and is arranged to move when the user inhales, such that the pin-like structures puncture the covering of the dry-powder compartment, causing the dry-powder compartment to be opened and the active drug powder to be withdrawn therefrom for inhalation by the user.

For example, the invention can be adapted for use with known dry-powder inhalation devices, such as disclosed in US Patent Application Publication No. 2013/0042864, by placing such pin-like structures at the upper or lower surface of the casing and placing the covered dry-powder compartment the on the elongated support panel that rotates within the casing. When the elongated support panel rotates towards the top surface of the casing, the covered dry-powder compartment is forced against the pin-like structures. Once the puncturable covering of the dry-powder compartment at the end of the elongated support panel strikes against the pin-like structures at the upper or lower surface of the casing, the needle- or pin-like structures puncture the puncturable covering the dry-powder compartment, thereby releasing the dry-powder from the compartment.

Alternatively, the invention can be adapted for use with known dry-powder inhalation devices, such as disclosed in US Patent Application Publication No. 2013/0042864, in an alternative manner, by placing such pin-like structures on the top or bottom surface of the elongated support panel that rotates within the casing and at the end thereof. When the elongated support panel rotates towards the top or bottom surface of the casing, it strikes the covering of the dry-powder filled compartment that is situated on the upper or lower surface of the casing. Once the pin-like structures at the end of the elongated support panel strike the puncturable covering, the needle- or pin-like structures puncture the puncturable covering the dry-powder compartment, thereby releasing the dry-powder from the compartment.

Modern improved inhalation devices use multi-dose blisters for drug delivery, mainly for diseases associated with the respiratory system. Some advantages of these inhalation devices are delivery of dose consistency and compliance. Some inhalation devices, such as those from MicroDose Therapeutx, Inc., claim potential control of exhaling into the device, piezo-electric mechanism for efficient delivery, and counting and protecting the user from taking repeated dose. However, the complexity of these devices and their validation is costly, and these devices are still not fool-proof delivery systems. In addition, the delivered drug amount is limited.

The single disposable inhaler described herein allows those controls without the requirement of a complex electric and/or chip to be developed for the drug. A simple package arrangement and day printing on the container does the trick. The production costs are low. Following its use, the patient can dispose of the inhaler. No cleaning or resting and cartridge refilling of the device is required.

BRIEF DESCRIPTION OF THE DRAWINGS

The subject matter regarded as the invention is particularly pointed out and distinctly claimed in the concluding portion of this specification. The invention, however, both as to organization and method of operation, together with objects, features, and advantages thereof, may best be understood by reference to the following detailed descriptions when read with the accompanying drawings in which:

FIG. 1 shows a perspective view of a first embodiment of the inhalation device;

FIG. 2 shows an exploded perspective view of an embodied inhalation device wherein the dry-powder compartment and needle-like structure are illustrated;

FIG. 3*a* shows a cross-sectional view of an embodied inhalation device wherein the dry-powder compartment and needle-like structure are illustrated;

FIG. 3*b* shows a cross-sectional view of an alternate embodied inhalation device of FIG. 3*a* wherein the dry-powder compartment and a plurality of needle-like structures are illustrated;

FIG. 4*a* shows a cross-sectional view of an embodied inhalation device, wherein the support panel is not blocking the airflow through said device;

FIGS. 4*b* and 4*c* show cross-sectional views of an embodied inhalation device wherein the ends of the support panel proximal and distal to the inlet, respectively, may block the airflow through the device;

FIG. 4*d* shows a further cross-sectional view of an embodied inhalation device, showing some of the powder emerging from the punctured dry-powder compartment of the device after the cover of the dry-powder compartment has been punctured by the needle-like structures;

FIG. 5 shows an exploded perspective view of an alternate embodied inhalation device wherein the dry-powder compartment and needle-like structure are illustrated;

FIG. 6*a* shows a cross-sectional view of the alternate embodied inhalation device wherein the dry-powder compartment and needle-like structure are illustrated;

FIG. 6*b* shows a cross-sectional view of an alternate embodied inhalation device of FIG. 6*a* wherein two dry-powder compartments and two needle-like structures are illustrated;

It will be appreciated that for simplicity and clarity of illustration, elements shown in the figures have not necessarily been drawn to scale. For example, the dimensions of some of the elements may be exaggerated relative to other elements for clarity. Further, where considered appropriate, reference numerals may be repeated among the figures to indicate corresponding or analogous elements.

DETAILED DESCRIPTION OF THE INVENTION

In the following detailed description, numerous specific details are set forth in order to provide a thorough understanding of the invention. However, it will be understood by those of ordinary skill in the art that the present invention may be practiced without these specific details. In other instances, well-known methods, procedures, components have not been described in detail so as not to obscure the present invention.

This invention, inter alia, takes advantage of flow energy of inspired air to disperse neat or formulated micronized particles packaged in a dosage form. The present invention provides a novel inhaler device, in which a principle mode of operation of the device is the production of a beating action within the device, which facilitates, or causes, the release of a dry-powder drug contained in a blistered compartment located within the device.

The devices, kits and/or methods of the present invention may be particularly suitable to dispense dry-powder substances to in-vivo subjects, including animal and, typically, human subjects. The dry-powder substance may include one or more active pharmaceutical constituents as well as biocompatible additives that form the desired formulation or blend.

As used herein, the term "dry-powder" is used interchangeably with "dry-powder formulation" and means the dry-powder can comprise one or a plurality of constituents or ingredients with one or a plurality of (average) particulate size ranges.

In some embodiments, individual dispensable quantities of dry-powder formulations can be a single ingredient or a plurality of ingredients, whether active or inactive. The inactive ingredients can include additives added to enhance flowability or to facilitate aerosolization delivery to the desired systemic target. The dry-powder drug formulations can include active particulate sizes that vary.

In some embodiments, the dry-powder may comprise any therapeutic agent such as, for example, a drug or vaccine.

In some embodiments, any drug or drugs that may be administered by inhalation and that are either a solid or may be incorporated in a solid carrier are envisioned for incorporation within the inhalers, kits and/or methods of this invention. In some embodiments, the drug will be a drug for the treatment of a Respiratory disease or condition. In some embodiments, such drugs may comprise bronchodilators, corticosteroids and drugs for the prophylaxis of asthma. Other drugs such as anorectics, anti-depressants, anti-hypertensive agents, anti-neoplastic agents, anti-cholinergic agents, dopaminergic agents, amyloid plaque treatment, protein and prion protein misfolding, neurodegeneration, narcotic analgesics, beta-adrenergic blocking agents, prostoglandins, sympathomimetics, tranquilizers, steroids, vitamins and/or hormones may be employed. Exemplary drugs include: Salbutamol, Terbutaline, Rimiterol, Fentanyl, Fenoterol, Pirbuterol, Reproterol, Adrenaline, Isoprenaline, Ociprenaline, Ipratropium, Beclomethasone, Betamethasone, Budesonide, Disodium Cromoglycate and analogs, Nedocromil Sodium, Ergotamine, Salmeterol, Fluticasone, Formoterol, Insulin, Atropine, Prednisolone, Benzphetamine, Chlorphentermine, Amitriptyline, Imipramine, Cloridine, Actinomycin C, Bromocriptine, Buprenorphine, Propranolol, Lacicortone, Hydrocortisone, Fluocinolone, Triamcinclone, Dinoprost, Xylometazoline, Diazepam, Lorazepam, Folic acid, Nicotinamide, Clenbuterol, Bitolterol, Ethinyloestradiol and Levenorgestrel. Drugs may be formulated as a free base, one or more pharmaceutically acceptable salts or a mixture thereof.

The dry-powder formulation can also include desired excipients. Examples of excipients include lactose and trehalose. Other types of excipients can also be employed, such as, but not limited to, sugars which are approved by the United States Food and Drug Administration ("FDA") as cryoprotectants (e.g., mannitol) or as solubility enhancers (e.g., cyclodextrine) or other generally recognized as safe ("GRAS") excipients.

Examples of diseases, conditions or disorders that may be treated or prevented with the inhalers, kits and/or methods of the invention include, but are not limited to, asthma, COPD (chronic obstructive pulmonary disease), viral or bacterial infections, influenza, allergies, and other respiratory ailments, as well as, diabetes, other related insulin resistance disorders and neurodegeneration. The dry-powder inhalant administration may be used to deliver locally acting agents such as antimicrobials, protease inhibitors, and nucleic acids/oligionucleotides as well as systemic agents such as peptides like leuprolide and proteins such as insulin.

For example, inhaler-based delivery of antimicrobial agents such as antitubercular compounds, proteins such as insulin for diabetes therapy or other insulin-resistance related disorders, peptides such as leuprolide acetate for treatment of prostate cancer and/or endometriosis and nucleic acids or oligonucleotides for cystic fibrosis gene therapy may be performed. See e.g. Wolff et al., Generation of Aerosolized Drugs, J. Aerosol. Med. pp. 89-106 (1994). See also U.S. Patent Application Publication No. 2001/0053761, entitled "Method for Administering ASPB28-Human Insulin", and U.S. Patent Application Publication No. 2001/0007853, entitled "Method for Administering Monomeric Insulin Analogs", the contents of which are hereby incorporated herein by reference in their entirety.

Typical dose amounts of the unitized dry-powder mixture dispersed in the inhaler will vary depending on the patient size, the systemic target, and the particular drug. Typical doses that can be delivered by the inhaler range from 10 µg to 10 mg. Some additional exemplary dry-powder drugs include, but are not limited to, albuterol, fluticasone, beclamethasone, cromolyn, terbutaline, fenoterol, β-agonists (including long-acting β-agonists), salmeterol, formoterol, cortico-steroids and glucocorticoids.

In certain embodiments, the administered bolus or dose can be formulated with an increase in concentration (an increased percentage of active constituents) over conventional blends. Further, the dry-powder formulations may be configured as a smaller administrable dose compared to the conventional doses. For example, each administrable dry-powder dose may be on the order of less than about 60-70% of that of conventional doses. In certain particular embodiments, using the active dispersal systems provided by certain embodiments of the dry-powder inhaler configurations of the instant invention, the adult dose may be reduced to under about 15 mg, such as between about 10 µg to 10 mg. The active constituent(s) concentration may be between about 5-10%. In other embodiments, active constituent concentrations can be in the range of between about 10-20%, 20-25%, or even larger, up to the case where only pure drug is delivered.

In certain particular embodiments, during dose dispensing, the dry-powder in a particular dose receptacle may be formulated as an active pharmaceutical constituent(s) substantially without additives (such as excipients). As used herein, "substantially without additives" means that the dry-powder is in a substantially pure active formulation with only minimal amounts of other non-biopharmacological active ingredients. The term "minimal amounts" means that the non-active ingredients may be present, but are present in greatly reduced amounts, relative to the active ingredient(s), such that they comprise less than about 10%, and preferably less than about 5%, of the dispensed dry-powder formulation, and, in certain embodiments, the non-active ingredients are present in only trace amounts.

In some embodiments, the therapeutic agent can be a biologic, which includes, but is not limited to, proteins, polypeptides, carbohydrates, polynucleotides, and nucleic acids. In some embodiments, the protein can be an antibody, which can be polyclonal or monoclonal. In some embodiments, the therapeutic can be a low molecular weight molecule. In addition, the therapeutic agents can be selected from a variety of known pharmaceuticals such as, but are not limited to: analgesics, anesthetics, analeptics, adrenergic agents, adrenergic blocking agents, adrenolytics, adrenocorticoids, adrenomimetics, anticholinergic agents, anticholinesterases, anticonvulsants, alkylating agents, alkaloids, allosteric inhibitors, anabolic steroids, antacids, anti-diarrheals, antidotes, anti-folics, antipyretics, anti-rheumatic agents, psychotherapeutic agents, neural blocking agents, anti-inflammatory agents, drugs that treat diseases associated with amyloidosis and peptide and protein misfolding, such as prion (mad cow disease), Alzheimer's and Parkinson's diseases, anti-helmintics, anti-arrhythmic agents, antibiotics, anticoagulants, antidepressants, anti-diabetic agents, anti-epileptics, antifungals, antihistamines, antihypertensive agents, anti-muscarinic agents, anti-mycobacterial agents, anti-malarials, antiseptics, antineoplastic agents, antiprotozoal agents, immunosuppressants, immunostimulants, anti-thyroid agents, antiviral agents, anxiolytic sedatives, bone and skeleton agents, astringents, beta-adrenoceptor blocking agents, cardiovascular agents, chemotherapy agents, corticosteroids, cough suppressants, diagnostic agents, diagnostic imaging agents, diuretics, dopaminergics, enzymes and enzyme cofactors, gastrointestinal agents, growth factors, hematopoietic or thrombopoietic factors, hemostatics, hematological agents, hemoglobin modifiers, hormones, hypnotics, immunological agents, anti-hyperlipidemic and other lipid regulating agents, muscarinics, muscle relaxants, parasympathomimetics, parathyroid hormone, calcitonin, prostaglandins, radio pharmaceuticals, sedatives, sex hormones, anti-allergic agents, stimulants, steroids, sympathomimetics, thyroid agents, therapeutic factors acting on bone and skeleton, vasodilators, vaccines, vitamins, and xanthines Anti-neoplastic, or anti-cancer agents, include but are not limited to, paclitaxel and derivative compounds, and other anti-neoplastics selected from the group consisting of alkaloids, anti-metabolites, enzyme inhibitors, alkylating agents and antibiotics.

Exemplary proteins, include therapeutic proteins or peptides, or carrier proteins or peptides, including GCSF, GMCSF, LHRH, VEGF, hGH, lysozyme, alpha-lactoglobulin, basic fibroblast growth factor (bFGF), asparaginase, tPA, urokin-VEGF, chymotrypsin, trypsin, streptokinase, interferon, carbonic anhydrase, ovalbumin, glucagon, ACTH, oxytocin, phosphorylase b, secretin, vasopressin, levothyroxine, phatase, beta-galactosidase, parathyroid hormone, calcitonin, fibrinogen, polyaminoacids (e.g., DNAse, alpha1 antitrypsin, polylysine, polyarginine), angiogenesis inhibitors or pro-immunoglobulins (e.g., antibodies), somatostatin and analogs thereof, casein, collagen, soy protein, and cytokines (e.g., interferon, interleukin and others), immunoglobulins, Exemplary hormones and hormone modulators include proinsulin, C-peptide of insulin, a mixture of insulin and C-peptide of insulin, hybrid insulin cocrystals, growth hormone, parathyroid hormone, luteinizing hormone-releasing hormone (LH-RH), adrenocorticotropic hormone (ACTH), amylin, oxytocin, luteinizing hormone, (D-Tryp6)-LHRH, nafarelin acetate, leuprolide acetate, follicle stimulating hormone, glucagon, prostaglandins, steroids, estradiols, dexamethazone, testosterone, and other factors acting on the genital organs and their derivatives, analogs and congeners.

Exemplary hematopoietic or thrombopoietic factors include, among others, erythropoietin, granulocyte colony stimulating factor (G-CSF), granulocyte-macrophage stimulating factor (GM-CSF) and macrophage colony stimulating factor (M-CSF), leukocyte proliferation factor preparation, thrombopoietin, platelet proliferation stimulating factor, megakaryocyte proliferation (stimulating) factor, and factor VIII.

Exemplary therapeutic factors acting on bone and skeleton and agents for treating osteoporosis include calcium, alendronate, bone GLa peptide, parathyroid hormone and its active fragments, histone H4-related bone formation and proliferation peptide and their muteins, derivatives and analogs thereof.

Exemplary enzymes and enzyme cofactors include: pancrease, L-asparaginase, hyaluronidase, chymotrypsin, trypsin, tPA, streptokinase, urokinase, pancreatin, collagenase, trypsinogen, chymotrypsinogen, plasminogen, streptokinase, adenyl cyclase, and superoxide dismutase (SOD).

Exemplary vaccines include Hepatitis B, Influenza, MMR (measles, mumps, and rubella), and Polio vaccines and others.

Exemplary growth factors include nerve growth factors (NGF, NGF-2/NT-3), epidermal growth factor (EGF), fibroblast growth factor (FGF), insulin-like growth factor (IGF), transforming growth factor (TGF), platelet-derived cell growth factor (PDGF), hepatocyte growth factor (HGF) and so on.

Exemplary agents acting on the cardiovascular system include factors that control blood pressure, arteriosclerosis, etc., such as endothelins, endothelin inhibitors, endothelin antagonists, endothelin producing enzyme inhibitors vasopressin, renin, angiotensin I, angiotensin II, angiotensin III, angiotensin I inhibitor, angiotensin II receptor antagonist, atrial naturiuretic peptide (ANP), antiarrythmic peptide and so on.

Exemplary factors acting on the central and peripheral nervous systems include opioid peptides (e.g. enkephalins, endorphins), neurotropic factor (NTF), calcitonin gene-related peptide (CGRP), thyroid hormone releasing hormone (TRH), salts and derivatives of TRH, neurotensin and so on.

Exemplary chemotherapeutic agents, such as paclitaxel, mytomycin C, BCNU, and doxorubicin.

Exemplary agents acting on the respiratory system include factors associated with asthmatic responses, e.g., albuterol, fluticazone, ipratropium bromide, beclamethasone, and other beta-agonists and steroids.

Exemplary steroids include, but are not limited to, beclomethasone (including beclomethasone dipropionate), fluticasone (including fluticasone propionate), budesonide, estradiol, fludrocortisone, flucinonide, triamcinolone (including triamcinolone acetonide), and flunisolide. Exemplary beta-agonists include, but are not limited to, salmeterol xinafoate, formoterol fumarate, levo-albuterol, bambuterol, and tulobuterol.

Exemplary anti-fungal agents include, but are not limited to, itraconazole, fluconazole, and amphotericin B.

Numerous combinations of active agents may be desired including, for example, a combination of a steroid and a beta-agonist, e.g., fluticasone propionate and salmeterol, budesonide and formoterol, etc.

The inhalers of this invention are dry-powder inhaler devices, comprising a casing, such as, for example, a rectangular or tubular shaped box or enclosure. In certain embodiments, the casing includes an elongated longitudinal axis, and includes a first terminus and a second terminus opposite the first terminus. The casing further includes an air inlet located at the first terminus of the casing and a powder delivery port located at the second terminus of the casing, said powder delivery port being located distal to the air inlet.

The term "casing" refers to, inter alia, the container comprising the various elements of the device as described herein. The casing may be of any appropriate material, including, in some embodiments, any plastic or other appropriate synthetic material, which may be prepared to conform to the desired structure and will contain or comprise the elements described herein. In some embodiments, the casing may comprise a Polycarbonate or HDPE.

The casing will include two openings placed at opposite ends of the casing. One such opening is the air inlet, which inlet is sufficient in size to facilitate air entry and exit therefrom. Another opening in the casing is a powder delivery port, which powder delivery port is positioned at an opposite end of the casing from that of the air inlet.

The powder delivery port is an opening, and is, generally, larger in size, in terms of overall area, than the size of the air inlet.

Referring now to FIG. 1, the air inlet 14 is positioned at one end or terminus of casing 10, whereas the powder delivery port 54 is at the opposite end or terminus of casing 10.

The casings of this invention may be prepared by any means and may include, for example, designs which include two halves of the casing, which may be hermetically and permanently sealed, or in some embodiments, the casing may be of a single piece, for example, as prepared by molding or other conventional means.

Figure 5:
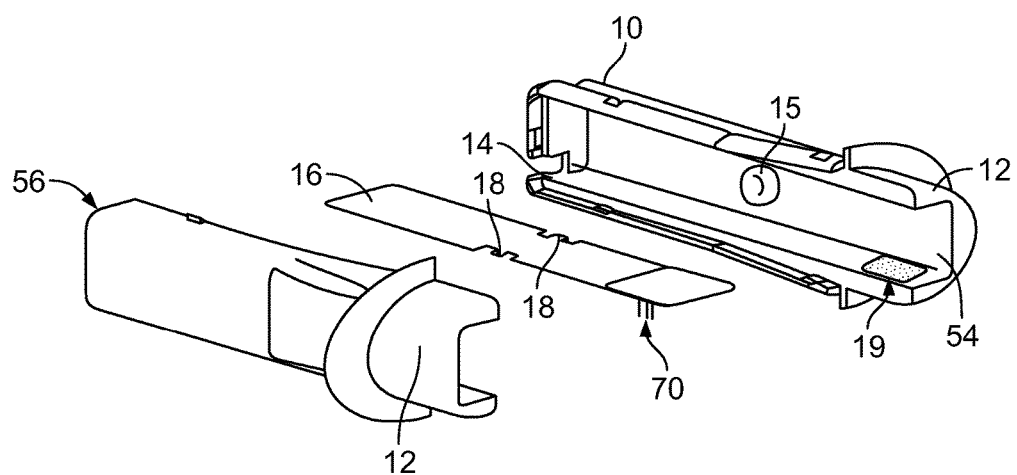

In some embodiments, the inhaler devices of this invention are suitable for inhalation delivery by mouth, or nasal delivery. According to one aspect, and in one embodiment, the powder delivery port 54 is partially enclosed by or attached to a mouthpiece 12 (see, e.g., FIGS. 1, 2 and 5), or in some embodiments, the delivery port 54 is partially enclosed by or attached to a nosepiece, which enables inhalation delivery via the mouth or nose.

In some embodiments, such choice between nasal or mouth delivery will reflect a consideration of the target area for delivery in the nasopharynx and other regions of the respiratory tree, or the particle size for delivery, or the age of the subject to which the inhaled powder is being administered, or a combination thereof.

In some embodiments, the air inlet 14 is positioned to be off center relative to a horizontal (i.e., longitudinal) axis, a vertical axis or a combination thereof of a side of the casing 10 containing the air inlet 14. For example, referring to FIGS. 4a-d, it is noted that the air inlet 14 is located in a lower half of side 56 relative to the longitudinal axis. Similarly, the air inlet 14 is located off-center relative to a vertical midline axis.

Figure 2:
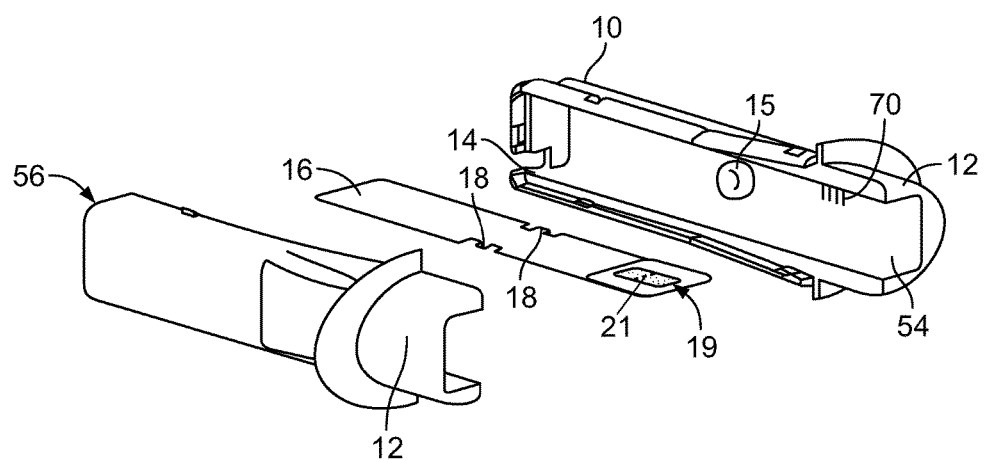

Referring to FIG. 2, the casing 10 of the dry-powder inhaler devices of the present invention further include an elongated support panel 16 located within an interior cavity of the casing 10. The elongated support panel 16 resembles an elongated plate, and includes a first terminus and a second terminus opposite the first terminus. In some embodiments, the first terminus is located proximally to the air inlet 14, and the second terminus is located proximally to the powder delivery port 54. In certain embodiments, the elongated support panel 16 is fitted, or arranged, within the casing 10 such that the elongated support panel 16 partially rotates, angles or pivots, within the casing 10 about a single axis, shown as pivot axis 18.

In some embodiments, the casing 10, the support panel 16, or a combination thereof is substantially rectangular. In some embodiments, the casing 10, the support panel 16, or a combination thereof is substantially cuboidal, or in some embodiments, the casing 10, the support panel 16, or a combination thereof is substantially columnar, or in some embodiments, the casing 10, the support panel 16, or a combination thereof is substantially oval, in shape.

Figure 3A:
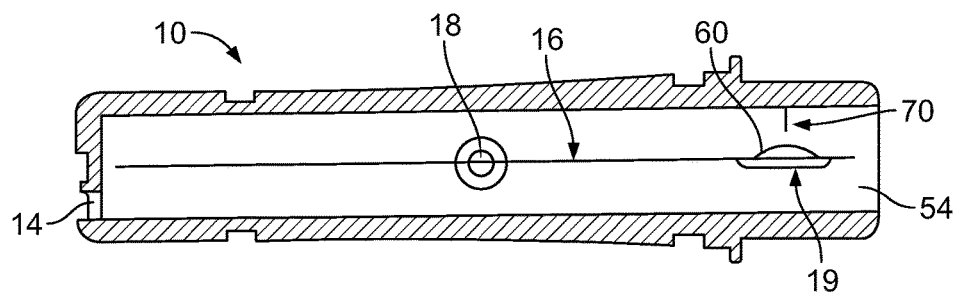
Figure 3B:
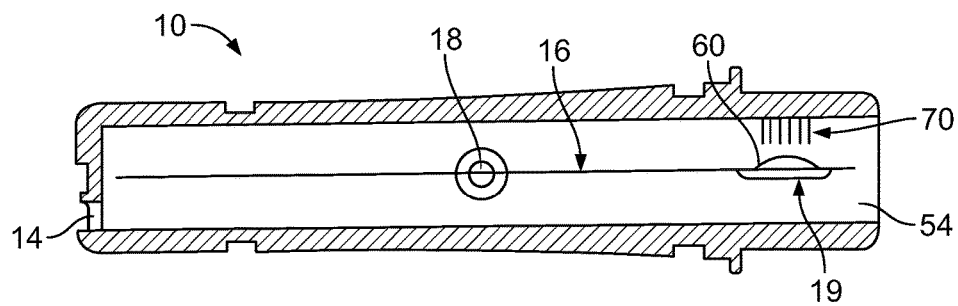

Referring to FIGS. 3a and 3b, the longitudinal axis of the support panel 16 is preferably oriented in parallel to the longitudinal axis of the casing 10.

In some embodiments, a typical size range for the casing 10 of the present invention is between 5 cm and 15 cm in length, and with height and width dimensions in the 0.5 cm-2 cm range. The length and width of support panel 16 are set to closer fit the inner dimensions of this casing 10. It should be noted that the size of the casing 10 is not a limitation on the device.

Referring now to FIGS. 2, 3a and 3b, in preferred embodiments of the invention, the elongated support panel 16 comprises at least one compartment 19, located proximally to the second terminus of the support panel 16, near the powder delivery port 54 when positioned within the casing 10 as herein described. In some embodiments, support panel 16 will comprise the same material as that of the compartment 19, which may be formed of aluminum or some other suitable material, or in some embodiments, support panel 16 will comprise a different material than that of the compartment 19. In some embodiments, the compartment 19 is contiguous in structure with that of support panel 16, for example it has an indent for containing the medicament. In some embodiments, the compartment 19 is bonded, welded or otherwise attached to support panel 16.

In some embodiments, the at least one compartment 19 is a cavity that is filled with dry powder medicament in an appropriate atmosphere and then sealed, e.g., by any suitable means as known in the art, such as is known in the field of packaging. In some embodiments, the dry-powder compartment 19 is covered and sealed by covering 60, such as aluminum or other known blister-pack type coverings, and sealed as known in the art. Cover 60 of compartment 19 keeps the powdered medicament dry and uncontaminated. In certain embodiments, cover 60 is capable of being punctured or ruptured by sharp device or object, to thereby allow the dry-powder 52 contained within compartment 19 to be released therefrom.

In certain embodiments, the casing 10 includes at least one sharp or pointed device 70 located on an internal surface thereof, proximal to the second terminus of the casing and near the powder delivery port 54. In preferred embodiments, as shown in FIGS. 2, 3a and 3b, the at least one sharp or pointed device 70 is a region of needle- or pin-like structures 70 that may include one or more fins, pins, needles, edges, or other type of sharp or pointed needle- or pin-like structures that extend from the casing 10 in a direction transverse (i.e., perpendicular) to a longitudinal axis of the casing 10. In preferred embodiments, the region of needle- or pin-like structures 70 is suitable for puncturing or rupturing the blister sealed compartment 19.

In some embodiments of the present invention, as shown in FIG. 3a, there is only one needle-like structure 70. In other embodiments, as shown in FIG. 3b, there are two or more (i.e., a plurality) of needle-like structures 70. In other embodiments of the present invention, a region, such as protruding surface, of casing 10 includes a series, comb or bristle of needle-like structures 70 (see, for example, FIG. 3b). In this embodiment, the shape of the comb of needle-like structures 70 may substantially replicate or mimic the shape of the cover 60 over compartment 19 such that, as the support panel 16 rotates and the cover 60 strikes the structures 70, the series of needle-like structures 70 may produce a series of puncture holes, or pores, over substantially the entire surface area of the cover 60.

In preferred embodiments, the cover 60 may be fabricated from any suitable material as known in the art, such as, from an aluminum material, for example, aluminum or aluminum foil, aluminized foil, although the cover 60 may be fabricated from any suitable material that seals compartment 19 and is easily punctured or ruptured by the needle- or pin-like structures 70.

The support panel 16 located within the casing 10 is elongated and has a length sufficient that each terminus can abut or strike an interior surface of the casing 10 when rotated, angled or pivoted. Indeed, the support panel 16 is positioned within the casing 10 such that a first terminus of the support panel 16 is located proximally to the air inlet 14 while a second terminus of said support panel 16 is located proximally to said powder delivery port 54, such that a long axis of the support panel 16 is oriented in parallel to a longitudinal axis of the casing 10. In preferred embodiments, airflow through the device (i.e., air flowing from air inlets 14 towards powder delivery port 54 upon user inspiration) causes said elongated support panel 16 to partially rotate or pivot within said casing 10 about pivot axis 18 such that the second terminus of said support panel 16 will strike the interior surface of the casing 10, on the upper and lower internal surfaces thereof.

Figure 4A:
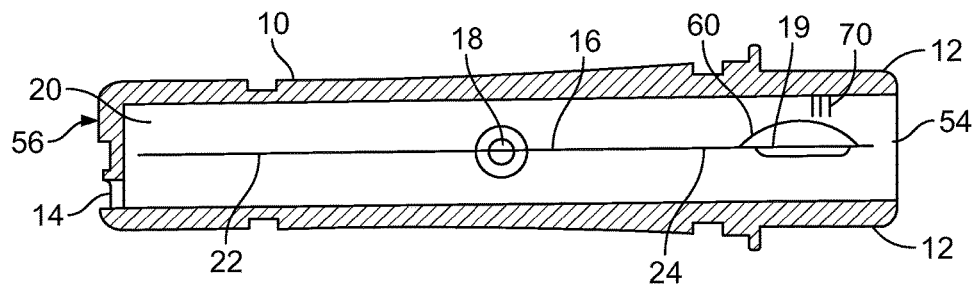
Figure 4B:
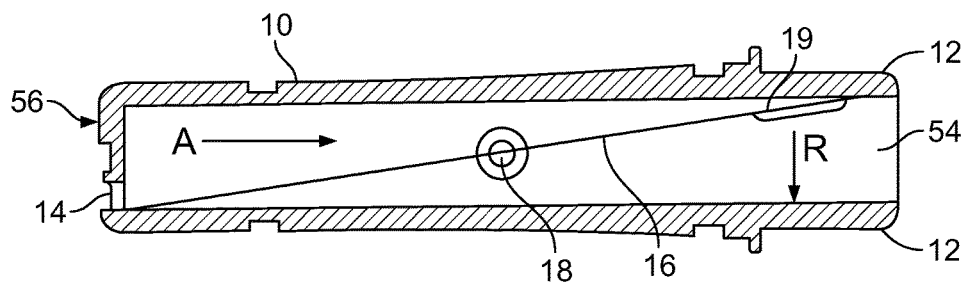
Figure 4C:
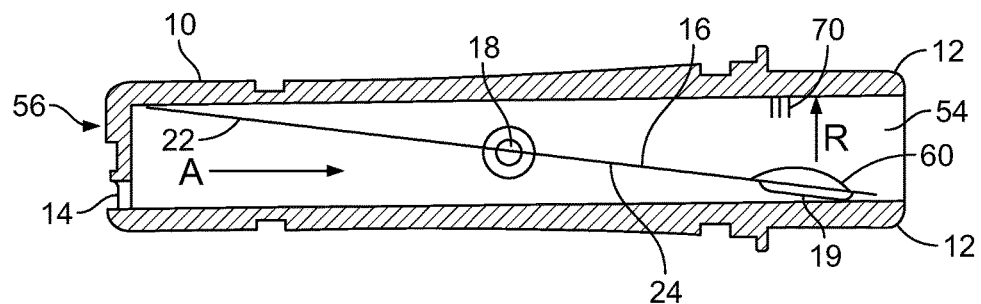

The principle of operation of an embodied device of the present invention is depicted in FIGS. 4a-d. A number of different possible states of the support panel 16 within the casing 10 are shown, as the support panel 16 partially rotates back and forth about pivot axis 18 due to an inhalation action, at the powder delivery port 54, which may be facilitated by the incorporation of a mouthpiece at its end. FIG. 4a shows a state in which the support panel is not blocking the airflow through the casing 10. Without being bound by theory, it is shown that the off-center positioning of the air inlet 14 creates turbulence in the area 20 between the inlet 14 and the portion 22 of the support panel 16 proximal to the air inlet 14. According to this aspect, the support panel 16 is tipped by the turbulence into one of the states shown in FIGS. 4b and 4c. Referring now to FIG. 4b, the support panel end 22 proximal to the air inlet 14 lowers, raising the support panel end 24 distal to the air inlet 14, resulting in some blocking of the airflow through the device. In one mechanism, the airflow (shown as "A"; FIGS. 4b and 2c) causes the support panel 16 to partially rotate, angle, pivot or rock in the direction shown by the arrow marked "R" (FIGS. 4b and 4c), which, in turn, causes the support panel 16 to partially rotate in an opposing direction, or flip to the configuration shown in FIG. 4c. Such partial rotation or flipping, may cycle (i.e., repeat), i.e. the airflow ("A") may cause the support panel 16 to flip back to its former state.

In some embodiments, such partial rotation, rocking or flipping of the support panel 16 within the casing 10 is accomplished due to a unique fitting of a lateral extension of the support panel 16, for example pivot axis 18 in FIG. 2, which is pivotally mounted within an appropriate housing, for example, 15 in FIG. 1b. In some embodiments, such casing 10 may also comprise a slit or rounded hole through a side wall thereof, into which such lateral extension may insert. Any other modification of the support panel 16 to allow for positioning of the support panel within the casing 10 and facilitating partial rotation of the support panel 16 may be considered as operable within this invention.

Figure 4D:
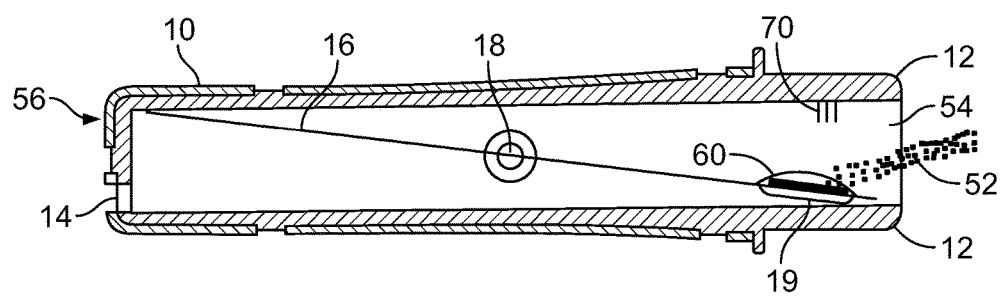

In preferred embodiments, a user's breathing action typically causes airflow through the device (i.e., air flowing from air inlets 14 towards powder delivery port 54 upon user inspiration), which causes said elongated support panel 16 to partially rotate or pivot within casing 10 about pivot axis 18 several times per second, in an up-and-down motion, thereby beating dry-powder compartment 19 against casing 10. In preferred embodiments, due to the alignment of dry-powder compartment 19 and the region of pin-like structures 70, the beating action of support panel 16 during inspiration causes the cover 60 covering dry-powder compartment 19 to repeatedly strike the region of pin-like structures 70, whereupon the needle-like structures 70 puncture or rupture the blister cover 60. As depicted in FIG. 4d, this repeated beating of dry-powder compartment 19 against structures 70 causes the rupturing of cover 60, which allows the dry powder medicament within dry-powder compartment 19 to be released therefrom and into the air flow space, from where it is inhaled into the user's throat and lung space.

Following repeat partial rotations, resulting in beating of the dry-powder containing compartment 19 distal to the air inlet 14 against one or more pin-like structures 70 provided on an internal surface of the casing 10, the powder contained within the compartment 19 emerges as free powder 52 into the airflow, which is drawn towards the powder delivery port 54 with mouthpiece 12. Without being bound by theory, as this free powder 52 emerges, it is disaggregated as a result of the sieving action of the holes or pores created in the cover 60 of compartment 19 by the action of the needle-like structures 70. In one embodiment, such hole-size for disaggregation to achieve dry-powder particles in the 1-5 micron diameter range is in the 10 micron to 70 micron range.

In certain embodiments, the pins, fins, edges, or needles 70 of the region puncture the cover 60, thereby or making holes therein or rendering the blister cover 60 porous.

In certain embodiments, the needles-like structures 70 are sized such as to create pores in the blister 60 of a size sufficiently large to enable the exit of the particles of dry-powder. In some embodiments, the pores are have a pore size ranging from about 20 to 50 microns, which in some embodiments, is ideally sized for the release of a dry-powder drug having a diameter of about 1-5 microns. For a 3 micron diameter particle, for example, the pore size may range from between about 6 microns and 150 microns, or in some embodiments, between about 10 microns and 80 microns or in some embodiments between about 20 microns and 60 microns.

In some embodiments, according to this aspect, dry-powder exit from the inhaler device of this invention is facilitated by the beating action, or abutment of the support panel against an interior surface of the casing 10, which results in powder egress from the holes or pores created in the cover 60 by the needle- or pin-like structures 70.

In other embodiments, the interior surface of the casing 10 may include two or more regions of needle-like structures 70. For example, casing 10 may include one region of needle-like structures 70 on a top interior surface thereof and one region of needle-like structures 70 on a bottom interior surface thereof. Additionally, in this embodiment, the inhaler may include two or more covered compartments 19. One covered compartment 19 located on an upper surface of support panel 16 and aligned with the region of needle-like structures 70 located on the upper interior surface of casing 10, and one covered compartment 19 located on the bottom surface of support panel 16 and aligned with the region of needle-like structures 70 located on the bottom interior surface of casing 10.

In the embodiments described above, the region of needle-like structures 70 is located on an interior surface of the casing 10, and the compartment 19 is located on support panel 16.

Figure 6A:
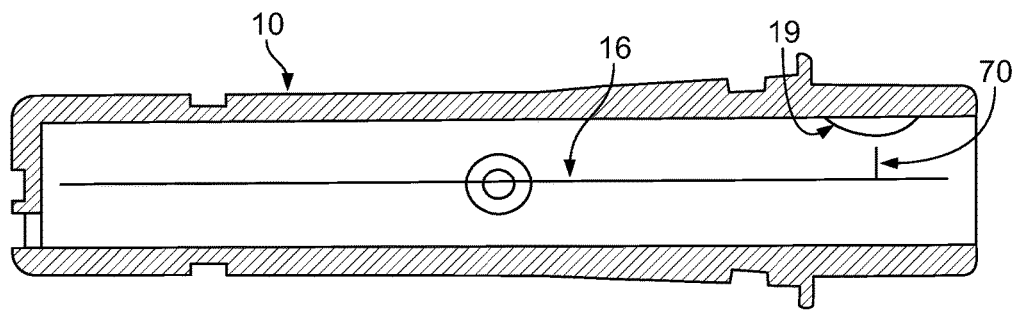

In other embodiments, support panel 16 may include the needle-like structures 70, and the interior surface of the casing 10 may include the dry-powder compartment 19. For example, it is possible to have one or more regions of needle-like structures 70 located on support panel 16 and the dry-powder compartment 19 located on an interior surface of casing 10 and aligned with the region of needle-like structures 70. For example, in certain embodiments, such as illustrated in FIG. 6a, support panel 16 may include a region of needle-like structures 70 protruding vertically upwards from a top surface of support panel 16, and aligned with a covered compartment 19 extending vertically downwards from a top interior surface of casing 10.

Figure 6B:
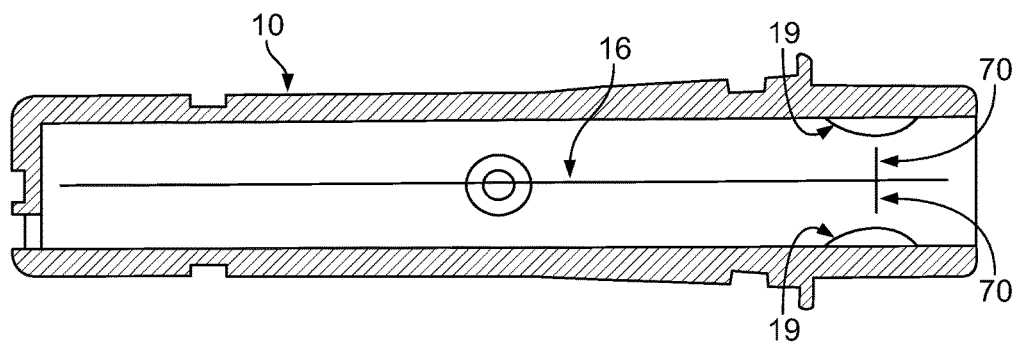

However, in other embodiments, such as illustrated in FIG. 6b, support panel 16 may include one region of needle-like structures 70 on a top surface of support panel 16 and one region of needle-like structures 70 on a bottom surface of support panel 16. Additionally, in this embodiment, the inhaler may include two or more covered compartments 19. One covered compartment 19 located on a bottom interior surface of casing 10 and aligned with the region of needle-like structures 70 located on the bottom surface of support panel 16, and one covered compartment 19 located on the top interior surface of casing 10 and aligned with the region of needle-like structures 70 located on the top surface of support panel 16.

As discussed above, the airflow through the device causes the support panel 16 to repeatedly rotate between the two states. Each time this occurs, the support panel end 24, comprising the needle- or pin-like structures 70 distal to the air inlet 14, beats against an internal surface 26 of the casing 10 containing the dry-powder containing compartment 19, causing the dry-powder compartment 19 to be punctured or ruptured by the needle- or pin-like structures 70 aligned with the cover 60, thereby causing the dry-powder drug within the compartment 19 to be released gradually from compartment 19.

The inhalers, kits and/or methods of the present invention, inter alia, are well suited to deliver two or more inhaled dry-powder drugs simultaneously while storing them separately.

From a chemical perspective, the co-storage of two or more drugs within the same physical compartment can be problematic as the two drugs may interact, especially if they have different pHs. From a regulatory standpoint, it may be necessary to prove that there is no such interaction over a long time period, and this can add significant expense to the regulatory approvals process.

In some embodiments, according this aspect of the invention, a technical challenge in the inhaler industry involving the storage of two or more drugs, which is potentially problematic for both chemical and regulatory reasons, is obviated by certain embodiments of this invention.

The assemblies of this invention may comprise, in some embodiments, one or more compartments, with each compartment comprising a dry-powder. In some embodiments, when the assemblies comprise more than one compartment, each compartment may comprise the same or different dry-powders.

In some embodiments, the support panel comprises two or three compartments containing a dry-powder. According to this aspect of the invention, and in some embodiments, the two or three compartments comprise two or three different dry-powders.

In some embodiments, as shown in FIG. 2, the support panel comprises a compartment containing at least one or two partitions 21, which partitions 21 create separate chambers in the compartment. According to this aspect of the invention, and in some embodiments, the separate chambers may contain different dry-powders.

In some embodiments, when the support panel 16 comprises two or more chambers or compartments 19, the support panel 16 may strike the protruding surface at a region between the two chambers or compartments 19, or in some embodiments, the interior surface may comprise multiple protruding surfaces such that each chamber or compartment will strike the interior surface at a region containing a protruding surface.

For example, in certain embodiments, each blistered compartment 19 on support panel 16 is aligned with a corresponding region of needle-like structures 70, or comb of needle-like structures 70.

In some embodiments, the present invention provides for a method of dispensing dry-powder from an inhaler, comprising facilitating airflow through a dry-powder inhaler device including any single or combined embodiments described herein, to cause the support panel to partially rotate within the casing about a single axis causing the covered compartment 19 to strike one or more needle- or pin-like structures 70, thereby puncturing the blister cover 60, releasing dry-powder from the compartment 19 to become entrained in the airflow, and dispensing dry-powder from the inhaler. FIG. 2 depicts an embodiment whereby a principle mode of operation of an embodied device of this invention results in the dispensing of a dry-powder from an inhaler of this invention, which represents an aspect of the methods of this invention.

In certain embodiments, the inhaler devices of this invention may be single use devices, which are preloaded with a desired dry-powder agent, at a desired dosage.

In some embodiments, according to this aspect, care is taken to ensure appropriate dry-powder containment within the blistered compartments of the inhaler devices of the present invention, prior to or between uses of the inhaler device.

It will be evident to those skilled in the art that the invention is not limited to the details of the foregoing illustrative embodiments and that the present invention may be embodied in other specific forms without departing from the spirit or essential attributes thereof.

The embodiments presented herein are, therefore, to be considered in all respects as illustrative and not restrictive of the scope of the invention, and the skilled artisan will appreciate the appropriate equivalents thereto, which are to be considered as part of this invention.

The invention claimed is:
1. An inhaler device comprising:
a casing having at least one pin structure protruding into an internal portion thereof;
an air inlet located proximal to a first terminus of the casing;
a delivery port located proximal to a second terminus of the casing and positioned distal to the air inlet; and
an elongated support panel comprising a first terminus and a second first terminus at opposite ends thereof and at least one compartment containing an inhalable medicament located proximal to the second terminus and hermetically sealed by a cover that is configured to be punctured by the at least one pin structure,
the support panel being rotatably mounted within an interior of the casing such that the support panel partially rotates within the casing about a single axis upon flowing of air through the casing from the air inlet to the delivery port upon inhalation by a user at the second terminus of the casing;
wherein inhalation by the user of air through the casing causes the partial rotation of the elongated support panel within the casing, causing the at least one compartment to strike the at least one pin structure, such that the at least one pin structure punctures the hermetically sealed cover and allows the medicament contained within the at least one compartment to become released into the air flowing through the device.

2. The inhaler device according to claim 1, wherein the compartment cover is made of aluminum or aluminum foil.

3. The inhaler device according to claim 1, wherein the casing, the elongated support panel, or a combination thereof is rectangular.

4. The inhaler device according to claim 1, wherein the support panel comprises at least two compartments containing an inhalable medicament.

5. The inhaler device according to claim 4, wherein the two or more compartments each houses a different inhalable medicament.

6. The inhaler device according to claim 1, wherein the compartment containing the inhalable medicament comprises at least one partition, creating at least two separate chambers in the compartment.

7. The inhaler device according to claim 6, wherein each of the at least two separate chambers houses a different inhalable medicament.

8. The inhaler device according to claim 1, wherein the inhalable medicament is a therapeutic agent in the form of a dry-powder.

9. The inhaler device according to claim 8, wherein the therapeutic agent is a drug or a vaccine.

10. A kit comprising at least one inhaler device according to claim 1.

11. A inhaler device comprising:
a casing having an air inlet and a powder delivery port located opposite the air inlet; and
an elongated support panel located within an interior of the casing and having at least one compartment containing a dry-powder medicament and being hermetically sealed by a cover;
wherein the elongated support panel is configured to partially rotate about a single axis within the casing upon inhalation by a user on the casing, resulting in air flowing through the device, the partial rotation causing the compartment to strike at least one pin structure protruding into an interior portion of the casing, thereby puncturing the hermetically sealed cover of the compartment and releasing the dry-powder into the air flowing through the device.

12. A method of administering an inhalable therapeutic agent to a subject, said method comprising:
providing a therapeutic agent inhaler device comprising:
a casing having an air inlet and a delivery port located opposite the air inlet, the casing comprising at least one pin structure protruding into an internal portion thereof; and
an elongated support panel located within an interior of the casing and having at least one compartment containing the therapeutic agent and being hermetically sealed by a cover;
wherein inhalation by a user of air through the casing causes the elongated support panel to partially rotate about a single axis within the casing, causing the compartment to strike against the at least one pin structure, thereby puncturing the hermetically sealed cover of the compartment and releasing the therapeutic agent into the air flowing through the casing.

* * * * *